(12) United States Patent
Hartman

(10) Patent No.: US 6,545,759 B1
(45) Date of Patent: Apr. 8, 2003

(54) TRANSVERSE INTEGRATED OPTIC INTERFEROMETER

(76) Inventor: Nile F. Hartman, 3958 Saint Georges Ct., Duluth, GA (US) 30096

( * ) Notice: Subject to any disclaimer, the term of this patent is extended or adjusted under 35 U.S.C. 154(b) by 0 days.

(21) Appl. No.: 09/451,287

(22) Filed: Nov. 30, 1999

(51) Int. Cl.[7] .................................................. G01B 9/02
(52) U.S. Cl. ....................................... 356/477; 356/481
(58) Field of Search ................................. 356/477, 481, 356/517; 385/12, 14; 250/227.19, 227.27, 227.14

(56) References Cited

U.S. PATENT DOCUMENTS

| | | |
|---|---|---|
| 4,694,276 A | 9/1987 | Rastegar |
| 4,900,112 A | 2/1990 | Kawachi et al. |
| 4,978,188 A | 12/1990 | Kawachi et al. |
| 5,091,983 A | 2/1992 | Lukosz |
| 5,270,789 A | 12/1993 | Falco et al. |
| 5,276,743 A | 1/1994 | Penner et al. |
| 5,473,722 A | 12/1995 | Sohler et al. |
| 5,500,734 A | 3/1996 | Spanner |
| 5,623,561 A | 4/1997 | Hartman |
| 5,646,729 A | 7/1997 | Koskinen et al. |
| 6,335,793 B1 * | 1/2002 | Freeman et al. ............. 356/477 |

FOREIGN PATENT DOCUMENTS

| | | |
|---|---|---|
| DE | 4419586 | 12/1995 |
| WO | WO 98/22807 | 5/1998 |

* cited by examiner

*Primary Examiner*—Frank G. Font
*Assistant Examiner*—Andrew H Lee
(74) *Attorney, Agent, or Firm*—Alfred H. Muratori; Wayne E. Nacker

(57) ABSTRACT

An interferometer for detecting a property of an environment includes a source of a beam of light and a first planar waveguide. The first planar waveguide has a first end, an opposite second end and a first interior surface. A first coupler is disposed adjacent the first end so as to be capable of coupling a first portion of the beam into the first planar waveguide. A second coupler is disposed adjacent the second end so as to be capable of de-coupling a second portion of the beam from the first portion of the beam and onto a first predetermined exit path. A first region is disposed along the first interior surface between the first coupler and the second coupler. The first region allows light to propagate therethrough as a first function of exposure to the environment disposed adjacent thereto. The interferometer also includes a second planar waveguide having a third end, an opposite fourth end and a second interior surface. The second planar waveguide is disposed substantially parallel to the first planar waveguide so that a first portion of the first interior surface and a second portion of the second interior surface define a cavity therebetween. A second region is disposed along the second interior surface, between a third coupler and a fourth coupler, that allows light to propagate therethrough as a second function, different from the first function. The third coupler is disposed adjacent the third end so as to be capable of coupling a third portion of the beam into the second planar waveguide. The fourth coupler is disposed adjacent the fourth end so as to be capable of de-coupling a fourth portion of the beam from the third portion of the beam and onto a second predetermined exit path. At least a portion of the second predetermined path is co-incident with at least a portion of the first predetermined path so as to form a combined beam. A phase difference detector that is responsive to the combined beam indicates a phase difference between the second portion of the beam and the fourth portion of the beam, so as to indicate the property of the environment.

18 Claims, 6 Drawing Sheets

TRANSVERSE INTEGRATED OPTIC INTERFEROMETER

BACKGROUND OF THE INVENTION

1. Field of the Invention

The present invention relates to optical devices and, more specifically, to an optical interferometric sensor.

2. Description of the Prior Art

Sensors for detecting and measuring absolute or relative values of physical quantities such as chemical or biochemical concentration, magnetic or electric field strengths, pressure, strain, temperature, and pH, for example, in an environment to which the sensor is exposed, are well known in the art. Prior art sensors include optic sensors which provide measured values directly or by means of transducers. Interferometric type optic sensors are highly sensitive. Such sensors employ an interferometer to provide information about a condition sensed. An interferometer is an instrument that splits light from an input source into two light beams and, after the light beams are caused to travel through different paths, recombines the two beams resulting in interference and an interference pattern. An analysis of the interference pattern provides a sensitive measure of the difference in effective path length of the two optical paths.

Integrated optic sensors are monolithic structures characterized by the integration of various optical components into a single optic waveguide construction. An integrated optic sensor is typically a thin-film device comprising a waveguide constructed on a single substrate, which generally provides other optical elements or components to diffract, refract or reflect different beam portions propagating in the waveguide for purposes of separating or combining them. Integrated optic technology is particularly useful in providing the optical elements heretofore associated with interferometric sensors employing separate and discrete optical components. The prior art now includes integrated optic sensors that incorporate a variety of components including lenses, sensing fields, and filters on a single substrate.

A typical integrated optic sensor comprises one or more channel waveguides fabricated as a planar construct on a substrate. A channel waveguide is a linear structure of typically small cross-section, on the order of several micrometers wide by several micrometers high, providing an optical path for a propagating light beam. The index of refraction of the channel waveguide is higher than the index of refraction of the surrounding or supporting substrate. A light source and possibly a coupling mechanism are provided to cause a light beam to propagate within the channel waveguide. The light source can be a laser, a light emitting diode (LED), or an incandescent light source. The propagating light beam passes through a sensing region of the channel waveguide which is reactive to particular conditions of the environment. The environment may cause changes in the propagation characteristics of the channel waveguide, such as a change in the refractive index. The change in the refractive index changes the effective optical path length through the channel region, thereby changing the phase of the light beam as it emerges from the channel waveguide. Alternatively, if the channel waveguide is not directly sensitive to a particular environment, it may be coated with a material that is reactive to the environment, or to a component thereof, causing a change in the refractive index the light beam encounters. An optical output beam from the sensor can therefore be used for measuring the relative or absolute value of the condition of the environment.

The optical input beam propagates through the waveguide in modes which satisfy Maxwell's equations. Maxwell's equations govern the electric and magnetic fields of an electromagnetic wave propagating through a medium. The modes may be characterized by the frequency, polarization, transverse field distribution and phase velocity of the constituent waves. In rectangular channel waveguides the modes are designated as $TE_{m,n}$ and $TM_{m,n}$ which are orthogonally polarized components of the light beam, transverse electric and transverse magnetic, respectively, with mode number indices m and n taking non-negative integer values. Each mode represents a different field distribution corresponding to the number of wave nodes across the waveguide in each direction. The allowed modes are determined in part by the configuration of the boundaries of the waveguide, which for integrated optic sensors are the interfaces between the substrate and waveguide, the environment and the waveguide, and the coating and the waveguide. Depending on the boundaries, the waveguide materials, the waveguide dimensions and the wavelength of the input light source, no modes, one mode, or more than one mode may be allowed to propagate through the waveguide.

Commercially available integrated optic interferometers include those utilizing a Mach-Zehnder interferometric technique. This technique is characterized by single mode propagation of two light beams through two light paths, then combining the two beams to produce an optical interference pattern. Generally, a Mach-Zehnder device receives a single input light beam which is then split by a beam splitter into two beams that are directed through two different channel waveguides. Changes in the optical path length of one of the waveguides are effected when the environment causes a change in its refractive index. The beams emerging from the channel waveguides are recombined to produce a single interfering beam which is indicative of the relative or absolute change caused by exposing the device to the environment.

Integrated optic interferometers employing the Mach-Zehnder configuration provide outstanding sensitivity and can be made in small sizes. These sensors, however, suffer in that they rely on two or more single-mode channel waveguides with typical cross-sectional dimensions of 0.1 $\mu$m by 3 $\mu$m each, making fabrication difficult and costly. Most importantly, the small size of the channels make efficient light coupling difficult to achieve with Mach-Zehnder interferometers. The light coupling difficulty makes this type of interferometer all but useless for many applications.

A second type of integrated optic interferometric sensor uses a planar waveguide as the planar construct. A planar waveguide is defined by only two (parallel) boundaries, rather than the four rectangular boundaries typical of a channel waveguide. In a planar waveguide, the propagating modes are designated as $TE_m$ and $TM_m$ (transverse electric and transverse magnetic, respectively), with the mode number index m taking non-negative integer values. As in the channel waveguide, the boundaries, the waveguide materials, the waveguide dimensions and the wavelength of the input light source determine whether no modes, one mode, or more than one mode may be allowed to propagate through the waveguide.

The descriptions herein of the prior art and of the invention use the term "optic" and "light," but it must be recognized that the techniques described are phenomena of electromagnetic radiation in general. Thus, the term "optic" and "light" herein should be read as referring to any electromagnetic radiation that meets whatever constraints are imposed by the characteristics of the various components of the sensor (such as the dimensions of the optical path) and the nature of the interaction between the sensor and properties of the environment to be sensed (such as the sensitivity of the sensor as a function of wavelength). Typically, the light will be in the visible or near-visible wavelength range.

Because prior art systems usually expose the active components of the sensor to different parts of the environment, in homogeneities in the environment can give rise to inaccurate results. For example, in a solution of a substance dissolved in a liquid one region may have a first concentration whereas an adjacent region may have a different concentration. Inaccuracies in the results of the sensor's analysis can result from the two arms of the interferometer probing regions with different concentrations. Furthermore, prior art systems provide no way to ensure that a consistent sample volume is being interrogated, which can give rise to inconsistent results. Thus, the prior art has the additional disadvantage of not constricting the portion of the environment being analyzed to a definite volume.

SUMMARY OF THE INVENTION

The disadvantages of the prior art are overcome by the present invention which, in one aspect, is an interferometer for detecting a property of an environment. The interferometer includes a source of a beam of light and a first planar waveguide. The first planar waveguide has a first end, an opposite second end and a first interior surface. A first coupler is disposed adjacent the first end so as to be capable of coupling a first portion of the beam into the first planar waveguide. A second coupler is disposed adjacent the second end so as to be capable of de-coupling a second portion of the beam from the first portion of the beam and onto a first predetermined exit path. A first region is disposed along the first interior surface between the first coupler and the second coupler. The first region allows light to propagate therethrough as a first function of exposure to an environment disposed adjacent thereto. The interferometer also includes a second planar waveguide having a third end, an opposite fourth end and a second interior surface. The second planar waveguide is disposed substantially parallel to the first planar waveguide so that a first portion of the first interior surface and a second portion of the second interior surface define a cavity therebetween. A second region is disposed along the second interior surface, between a third coupler and a fourth coupler, that allows light to propagate therethrough as a second function, different from the first function. The third coupler is disposed adjacent the third end so as to be capable of coupling a third portion of the beam into the second planar waveguide. The fourth coupler is disposed adjacent the fourth end so as to be capable of de-coupling a fourth portion of the beam from the third portion of the beam and onto a second predetermined exit path. At least a portion of the second predetermined path is co-incident with at least a portion of the first predetermined path so as to form a combined beam. A phase difference detector that is responsive to the combined beam indicates a phase difference between the second portion of the beam and the fourth portion of the beam, so as to indicate a property of the environment.

Another aspect of the invention is a method of manufacturing an interferometric sensor. A first waveguide is applied onto a first surface of a first substrate so that the first waveguide has a first end and an opposite second end. A first coupler is disposed adjacent the first end and a second coupler adjacent the second end. A first treatment is applied to a portion of the first waveguide. The first treatment allows light to propagate through a portion of the first waveguide as a first function of exposure to a property of an environment adjacent the portion of the first waveguide. A second waveguide is applied onto a second surface of a second substrate so that the second waveguide has a third end and an opposite fourth end. A third coupler is disposed adjacent the third end and a fourth coupler adjacent the fourth end. The first substrate is disposed substantially parallel to the second substrate so that the first coupler and the third coupler both lie on a first common optical path and so that the second coupler and the fourth coupler both lie on a second common optical path. The first common optical path and the second common optical path are at an angle to the direction of the first waveguide and the second waveguide. The first surface and the second surface face each other and define a cavity, having a width, therebetween.

Other aspects of the invention are methods of supporting analysis of a portion of an environment in an interferometric sensor in which the portion of the environment is subjected to an oscillating field that influences one or more components of the environment during the analysis.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
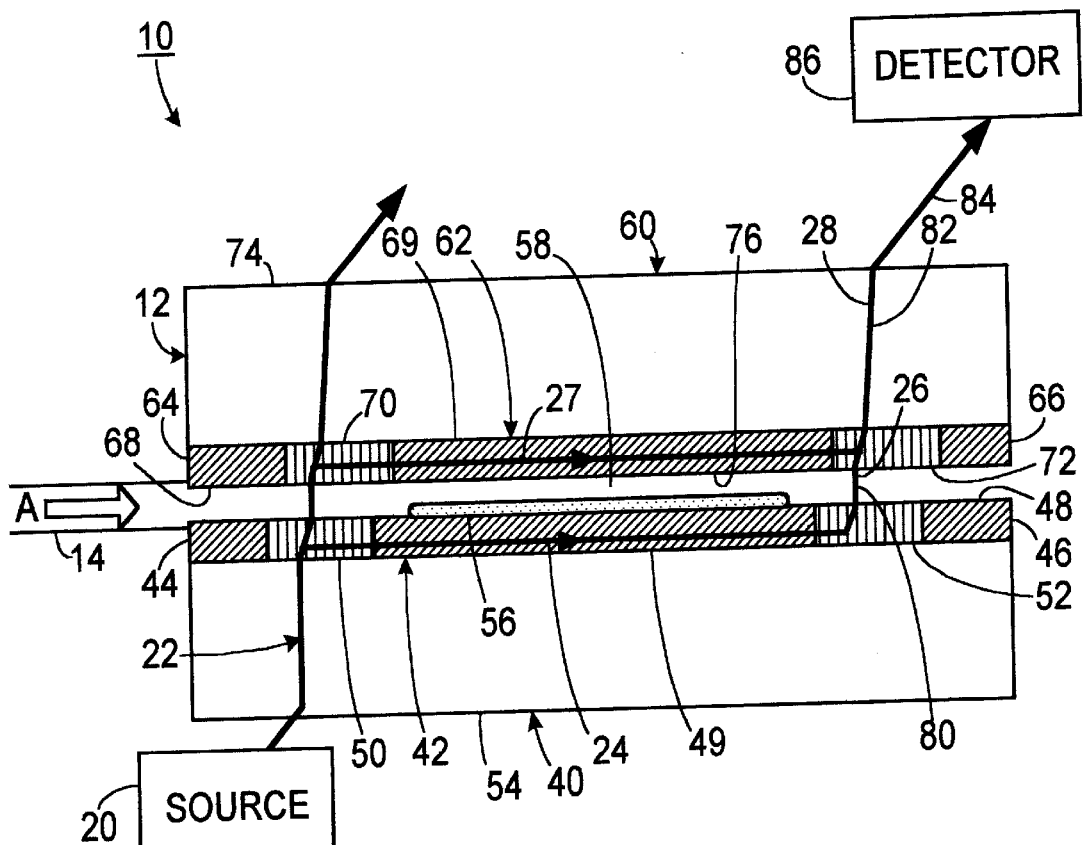
FIG. 1A is a cross-sectional view of a first embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

In the disclosure that follows, U.S. Pat. No. 5,623,561 (the '561 patent), issued to Hartman, is hereby incorporated by reference. The '561 patent shows, inter alia, details relating to the fabrication and use of interferometric sensors and integrated optic devices.

As shown in FIG. 1A, one simple embodiment of the invention is an interferometer 10 for detecting a property of an environment that includes a source 20 of a beam 22 of light and an integrated optic sensor 12. The property of the environment could include a component of a substance, but could also include other properties, such as the strength of fields, etc. The integrated optic sensor 12 includes a first unit 40 and an opposite second unit 60. In one embodiment, the source 20 could be a laser diode. The source 20 could also be a fiber optic pig tail, a light-emitting diode (LED) or a diode laser integrated into the body of the substrate, or a diode laser or an LED could be fabricated directly on the surface of the waveguide. Further, beam shaping elements, such as lenses, could enhance the coupling efficiency and uniformity of the beam.

The first unit includes a first substrate 54 and a first planar waveguide 42 having a first end 44, an opposite second end 46, a first interior surface 48, and a first exterior surface 49 that is adjacent the first substrate 54. The first substrate 54 could include a glass material (e.g., silicon dioxide, titanium dioxide, tantalum pentoxide, fused silicon), silicon, an alumina-gallium-arsenide material, or any other integrated optic material that is substantially transparent to the beam 22. A first coupler 50 (e.g., a diffraction grating) is disposed adjacent the first end 44 so as to be capable of coupling a first portion 24 of the beam 22 into the first planar waveguide 42.

A second coupler 52 is disposed adjacent the second end 46 so as to be capable of decoupling a second portion 26 of the beam 22 from the first portion 24 of the beam 22 and onto a first predetermined exit path 80. A first region 56 is disposed along the first interior surface 48 between the first coupler 50 and the second coupler 52 that allows light to propagate therethrough as a first function of exposure to the environment disposed adjacent thereto. Surface treatments that could be used to form the first region 56 include covalent attachment of antibodies, polymer films or reactive surface chemistries. (See, the '561 patent, column 13, line 31-column 14, line 59, for more details relating to the surface treatments.)

The second unit 60 includes a second substrate 74 and a second planar waveguide 62 having a third end 64, an opposite fourth end 66, a second interior surface 68 and an opposite second exterior surface 69. The second planar waveguide 62 is disposed substantially parallel to the first planar waveguide 42 so that a first portion of the first interior surface and a second portion of the second interior surface define a cavity 58 therebetween. A second region 76 is disposed along the second interior surface 68 between a third coupler 70 and the fourth coupler 72. The second region 76 allows light to propagate therethrough as a second function, different from the first function. The second region 76 may also include a special treatment that reacts to the environment, or it may simply comprise the untreated surface of the waveguide and any cladding applied thereto.

The third coupler 70 is disposed adjacent the third end 64 so as to be capable of coupling a third portion 27 of the beam 22 into the second planar waveguide 62. The fourth coupler 72 is disposed adjacent the fourth end 66 so as to be capable of de-coupling a fourth portion 28 of the beam 22 from the third portion 27 of the beam 22 and onto a second predetermined exit path 82. At least a portion of the second predetermined path 82 is coincident with at least a portion of the first predetermined path 80 so as to form a combined beam 84. As used herein, two co-incident beams would be co-linear and overlapping.

When the property of the environment reacts with the first region 56, the optical path length of the portion 24 of the beam 22 passing through the first planar waveguide 42 becomes different from the optical path length of the portion 27 of the beam 22 passing through the second planar waveguide 62. Thus, the interference pattern formed in the combined beam 84 is altered as a function of the reactance of the first region 56 with the property of the environment. A phase difference detector 86 is disposed so as to be responsive to the combined beam 84. The phase difference detector 86 indicates a phase difference between the second portion 26 of the beam 22 and the fourth portion 28 of the beam 22, thereby indicating the property of the environment. The phase difference detector 86 could be a light detector (or an array of light detectors) such as a silicon photo diode or a charge coupled device (CCD), such a detector would generate an electronic signal corresponding to the phase difference.

The sample being analyzed may be inserted through an entry 14 to the cavity 58, moving in direction A. In alternative embodiments, the device 10 could be used to detect a property of an environment other than the composition of a substance. For example, if an electrically reactive substance were disposed in the cavity 58 (possibly being sealed therein) and if the cladding on the second region shields the second region 76 from the electrically reactive substance, then the device 10 could be used to measure local electric field strength. Other examples of such embodiments include measuring magnetic field strength, measuring radiation intensity and even measuring acceleration. For example, if relatively dense particles were suspended in a relatively less dense medium and placed in the cavity 58, then acceleration in one direction would concentrate the particles in the opposite direction. If such particles are concentrated adjacent the first region 56, then the effect on the propagation of the first portion 24 of the beam 22 as a result of such concentration would indicate the amount of acceleration. It is intended that all such embodiments fall within the scope of the invention.

In the simplest embodiment, a single mode beam 22 (either TE or TM) is coupled into the first planar waveguide 42. However, in more complex embodiments, multiple modes of the beam 22 (e.g., multiple TE, multiple TM, or a mixture of TE and TM) may be coupled into the first planar waveguide 42. If N modes are coupled into the first planar waveguide 42, then N interference patterns will be generated, each decoupled at a slightly different angle. Each mode will interfere with its counterpart (i.e., $TE_0$ with $TE_0$, $TM_1$ with $TM_1$, etc.). One reason for doing this is that the different modes will measure the same property, but with different sensitivities. The most sensitive combination would provide the highest resolution. Combining a range of resolutions can simplify signal processing problems associated with the periodic nature of interferometer outputs. The output from a sufficiently low resolution combination would not extend beyond one period, providing an unambiguous (albeit relatively low resolution) measurement across the entire dynamic range.

Figure 1B:
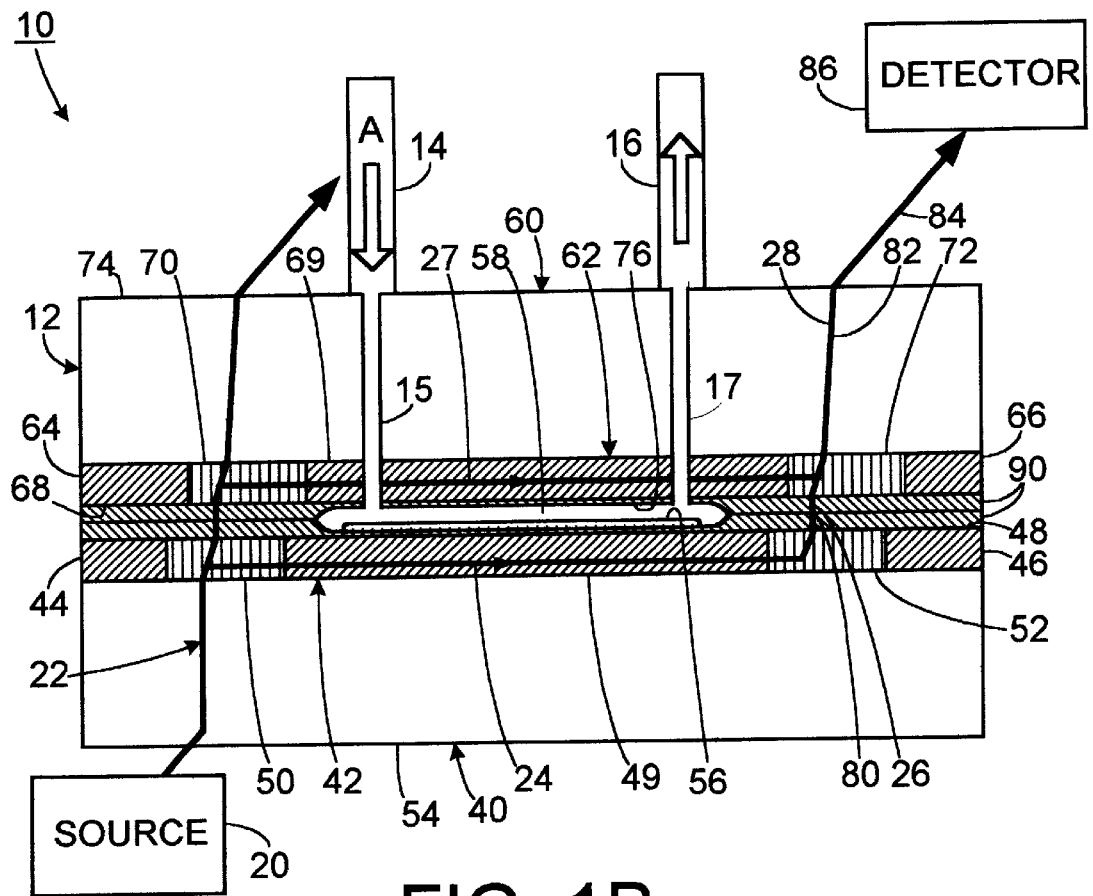
FIG. 1B is a cross-sectional view of the embodiment of FIG. 1A, modified to include cladding.
Figure 1C:
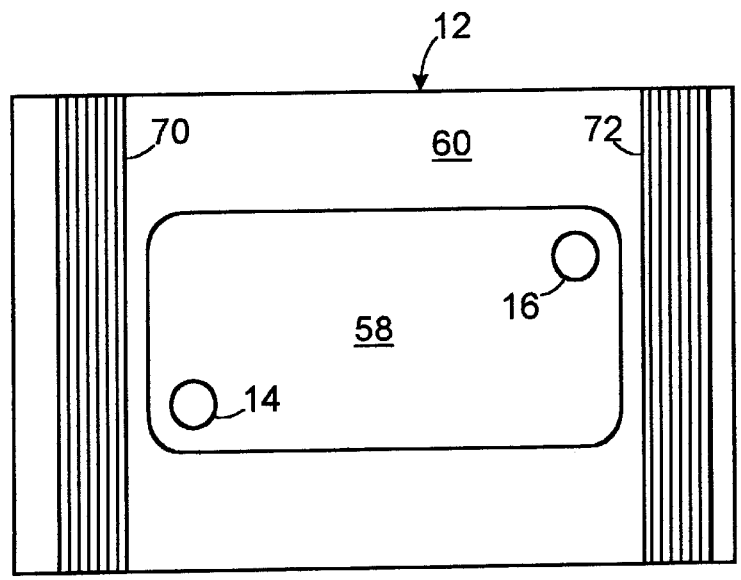
FIG. 1C is a top plan view of the embodiment shown in FIG. 1B.

FIGS. 1B–1C show a slightly more complex embodiment in which cladding 90 is added to cover the waveguides 42 and 62. The cladding 90 has a known index of refraction, thereby ensuring that the beam 22 propagates through the waveguides 42 and 62 with known characteristics and reducing the effect of the sample being tested on every variable except its interaction with the first region 56. The cladding 90 also serves to isolate the couplers 50, 52, 70 and 72 from the environment being analyzed so that the beam is not directly exposed to the sample. This feature ensures that the result of a test reflects only the sample's interaction with the first region 56 and not direct interaction between the beam 22 and the substance or property of the environment, being analyzed.

In the embodiment shown in FIGS. 1B–1C, the cladding 90 prevents direct entry of the sample into the cavity 58. Therefore, an entry hole 15 must be formed in one of the units 40 or 60 to couple the sample entry 14 to the cavity 58 and an exit hole 17 must be formed to couple the cavity 58 to the sample exit 16. As shown in FIG. 1B, a top view, the entry 14 should be disposed at one end of the cavity 58 and the exit should be disposed oppositely so that as the sample flows into the cavity 58 in direction A, it will flow through the cavity without forming any stagnant pockets. This ensures a uniform concentration of the sample being analyzed.

The first region 56 could simply be a region where the first waveguide 42 is exposed directly to the substance (or part of the environment) being analyzed. In such a case, the first function would be determined as a result of changes in the index of refraction of the sample in the cavity 58 at or near the first region 56. The first region 56 could also be a region where the first waveguide 42 is fabricated with a treatment that reacts with the environment in the cavity 58 so as to change the optical path length of the first portion 24 of the beam 22 passing through the first region 56. For example, the first region 56 could comprise a chemically reactive compound that is grown on the first waveguide 42 (e.g., epitaxially, through chemical vapor deposition, ion implantation, sputtering, or solution deposition) to form a chemically reactive film thereon. Such a film will react with a sample in the cavity 58 so as to change the index of refraction of the first region 56.

Although the figures show diffraction gratings used to couple and decouple light into and out of the planar waveguides, it is understood that many other configurations for coupling and decoupling light from waveguides could be employed in the invention. For example, direct butt-coupling or total internal reflection mirrors could be used. Alternatively, the light source and detector could be integrated into the body of the substrate or fabricated directly on the surface of the waveguide. (See, the '561 patent, column 10, line 35, for a discussion of alternated in-coupling. See, column 16, line 5 for a discussion of alternate out-coupling.)

Figure 2A:
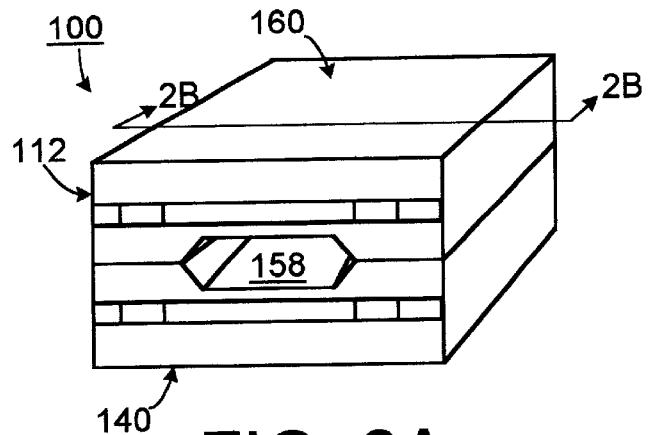
FIG. 2A is a top perspective view of a second embodiment of the invention.
Figure 2B:
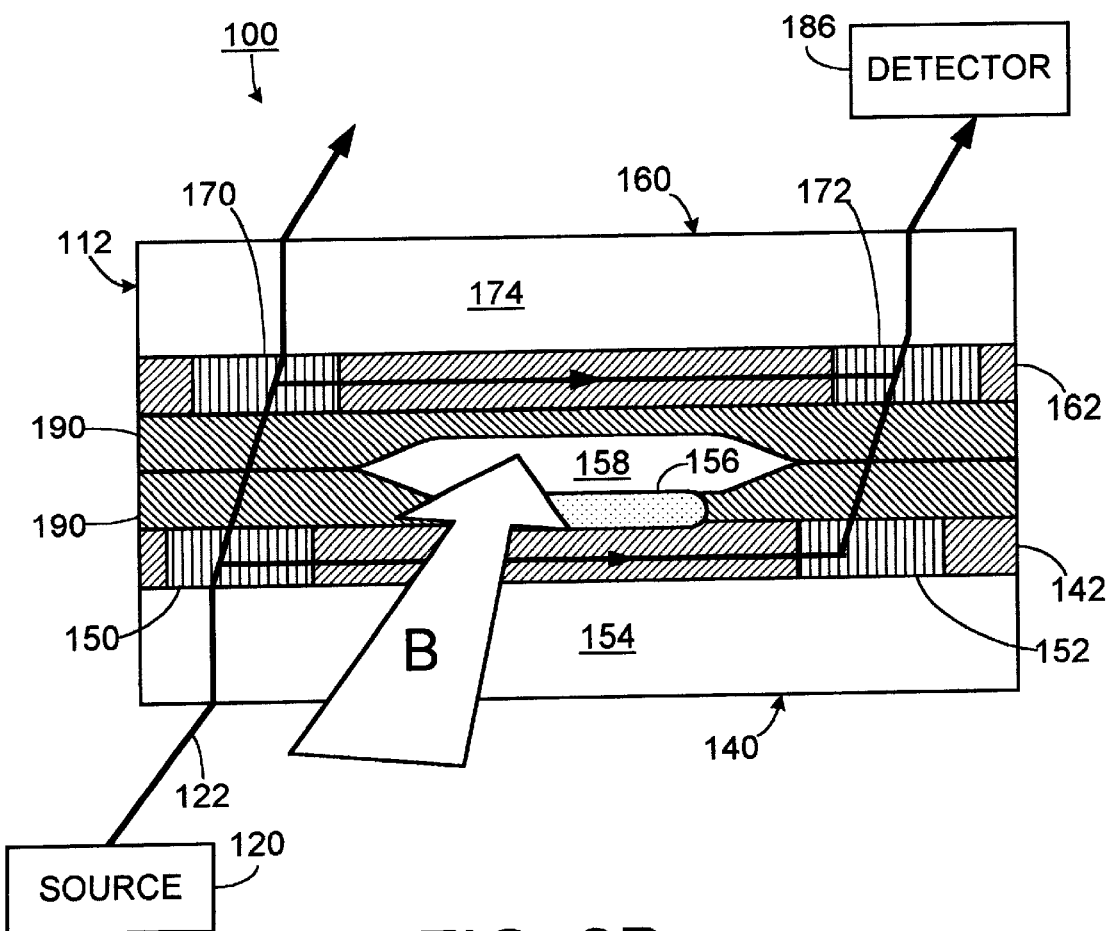
FIG. 2B is a cross-sectional view of the embodiment shown in FIG. 2A, taken along lines 2B—2B.

As shown in FIGS. 2A and 2B, one embodiment 100 of the invention is an interferometer 112 that includes a cavity 158 that runs at an angle to the direction of the light beam 122. The interferometer 112 includes a lower unit 140 and an opposite upper unit 160. The lower unit 140 includes a substrate 154, upon which is disposed a waveguide 142 and two diffraction gratings 150 and 152. A reactive treatment 156 may also be included on the lower waveguide 142. Similarly, the upper unit 160 includes a substrate 174, upon which is disposed a waveguide 162 and two diffraction gratings 170 and 172. A source 120 generates a beam 122 and a detector 186 detects the beam 122. As with the embodiments disclosed above, waveguide 162 may also include a special treatment that reacts to the environment, or it may simply comprise the untreated surface of the waveguide and any cladding applied thereto.

The cavity 158 is formed by carefully depositing the cladding 190 on each waveguide 142 and 162. The cavity 158 is arranged so that a sample may be passed into the interferometer in direction B. This embodiment 100 offers two advantages: (1) the beam 122 never comes in contact with the sample flowing in direction B, thereby reducing unwanted effects on the beam 122; and, (2) it is not necessary to form an entry hole and an exit hole through one of the substrates.

In most applications the waveguides 142 and 162 are separated by about 10 to 200 microns. As can be seen in FIG. 2B, precise control of the separation of the waveguides 142 and 162 and the dimensions of cavity 158 can be achieved by controlling the deposition of the cladding 190 onto the waveguides 142 and 162.

Figure 3:
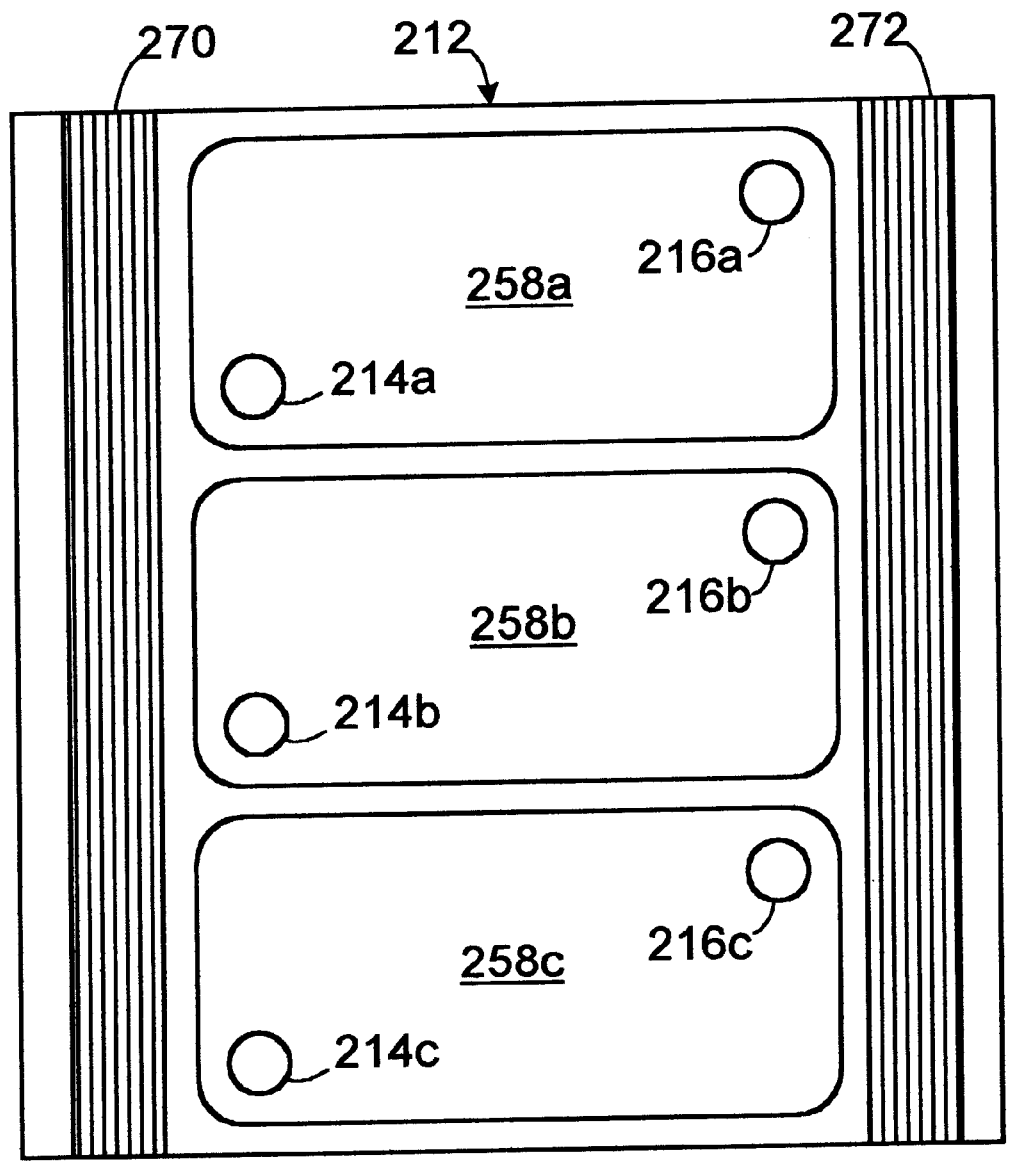
FIG. 3 is a top plan view of an embodiment that includes multiple cavities.

As shown in FIG. 3, it is possible to fabricate several interferometers on a single substrate 212. The substrate 212 could be fabricated to include a single coupler 270 and a single decoupler 272. By properly masking the fabrication of the cladding, a single common cavity or multiple separate cavities 258a–c (as shown) could be formed on the substrate 212. Each cavity 258 would have an independent input 214a–c and an independent output 216a–c. In this way, one sample could be input to cavity 258a, while a different sample could be input to cavity 258b and so on. Alternatively, each cavity 258a–c could have a different treatment (each treatment being reactive to a different property) and the inputs 214a–c could be fed by a common source. In these configurations, a single sample could be tested for several different properties at any given time, or multiple samples could be tested for the same property.

Figure 4A:
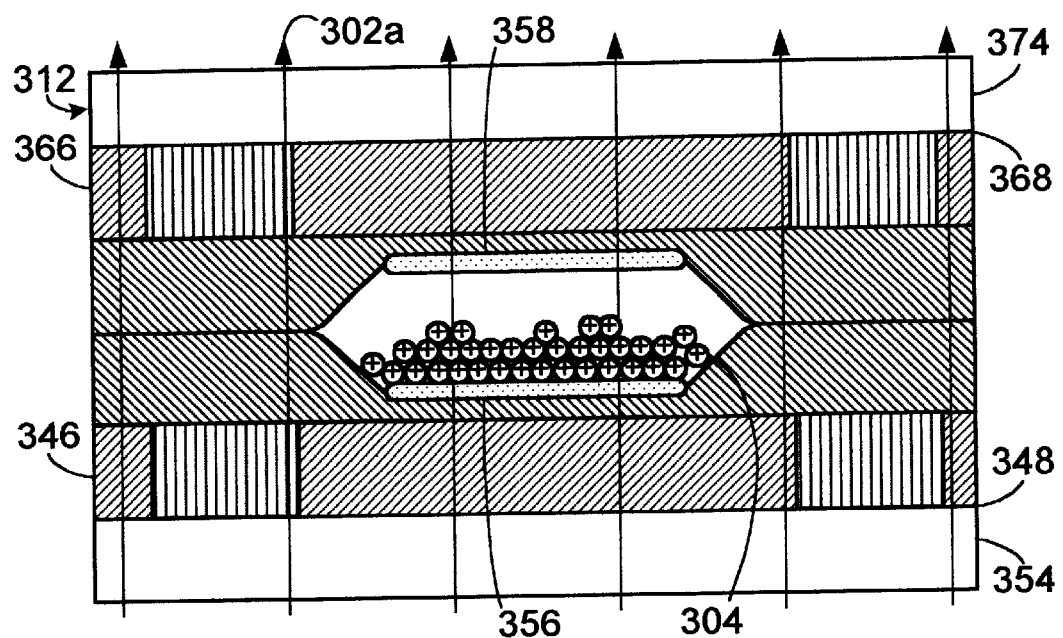
FIG. 4A is a cross-sectional view of an embodiment that is sensitive to a first electrical field.
Figure 4B:
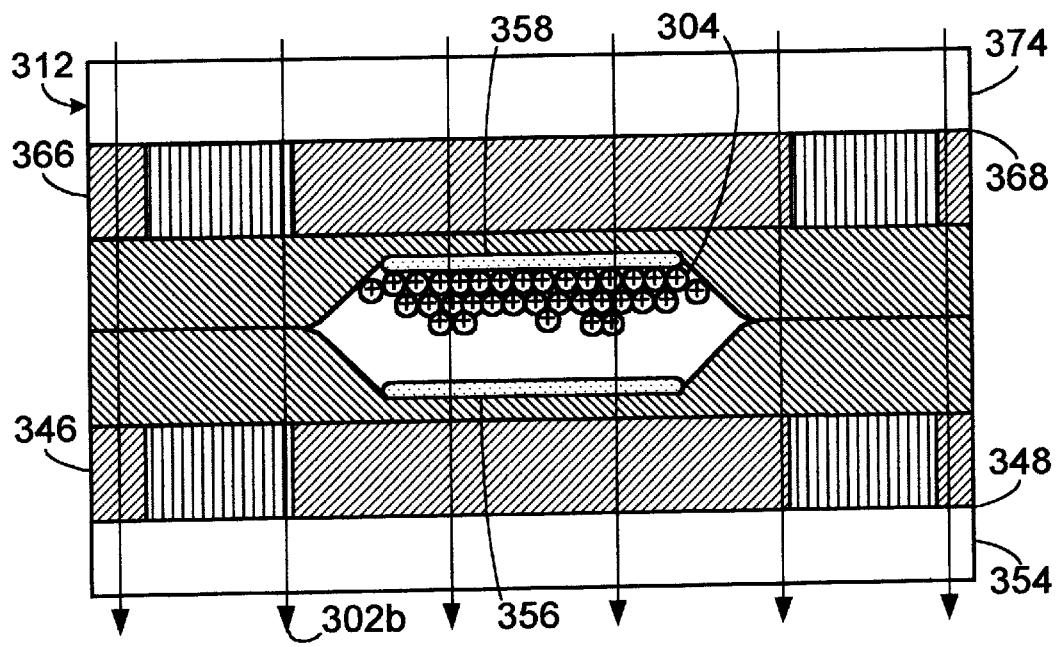
FIG. 4B is a cross-sectional view of the embodiment of FIG. 4A, wherein the electrical field has been reversed.

As shown in FIGS. 4A and 4B, an embodiment 312 of the invention designed for added sensitivity in analysis of a substance takes advantage of the fact that the closer a component of the sample is to the waveguide 346 and 366 surface, the stronger is the impact of that component on the propagating beam. For example, if the sample being analyzed includes charged components 304, application of an electric field (as shown by field lines 302a, in FIG. 4A, and field lines 302b corresponding to a reversed electric field in FIG. 4B) would draw the charged components 304 toward one of the poles of the field and, thus, to one of the waveguide 346 and 366 surfaces. As shown in FIG. 4A, if the charged components 304 move closer to the first waveguide 346, they must simultaneously move further away from the second waveguide 366. The effect is to strengthen the impact on the beam in the reactive region 356 of the first waveguide 346 (retarding its phase) and at the same time to weaken the impact on the beam in the reactive region 358 of the second waveguide 366 (accelerating its phase). Thus, the impact on the relative phase of the two beams could be twice what it would be for other interferometer configurations. As further shown in FIGS. 4A and 4B, reversing the electric field 302b causes the charged components to be driven away from the first waveguide 346 and toward the second waveguide 366. This could be done with an alternating current, the frequency of which being slow enough to correspond to the travel time of the components 304. Such a configuration could be used to increase the accuracy of the sensor by eliminating noise, with the oscillating field serving as a reference for phase-lock detection. These features could be used, for example, for electrophoresis. One means of applying the electric field is by use of optically transparent and electrically conductive thin film structures. For example, an indium tin oxide (ITO) layer film could be deposited between the substrate and waveguide layers of both the upper unit and lower unit. Similarly, an oscillating magnetic field can be employed in a system in which paramagnetic components are included in the sample.

In another embodiment, enhanced diffusion may be effected through use of an oscillating electromagnetic field and a selective treatment. To the extent that components of the test sample (such as biomolecules) are charged or paramagnetic, an oscillating electric or magnetic field will alternately pull them toward, then push them away from, the waveguide surfaces. Non-specific (interferent) components will simply oscillate in and out of the sensing volumes above the waveguide surfaces, resulting in a net zero signal over time scales long compared to the oscillation period. However, specific (target) components of the test sample will be pulled toward the waveguide surfaces and captured in the sensing volumes if there is an appropriate selective treatment, resulting in a sustained net signal. The purpose is to enhance the rate at which target components are transported to the surface beyond that which is possible with unaided diffusion. Furthermore, as previously described, the oscillating field can serve as a reference for phase-lock detection to enhance signal processing. These features could be used, for example, for immunoassays and nucleic acid detection. While these enhanced diffusion and signal processing mechanisms are disclosed in association with the interferometric sensor described above, it is intended that these aspects of the invention could be applied to many other types of interferometric sensors without departing from the scope of the invention.

Figure 5A:
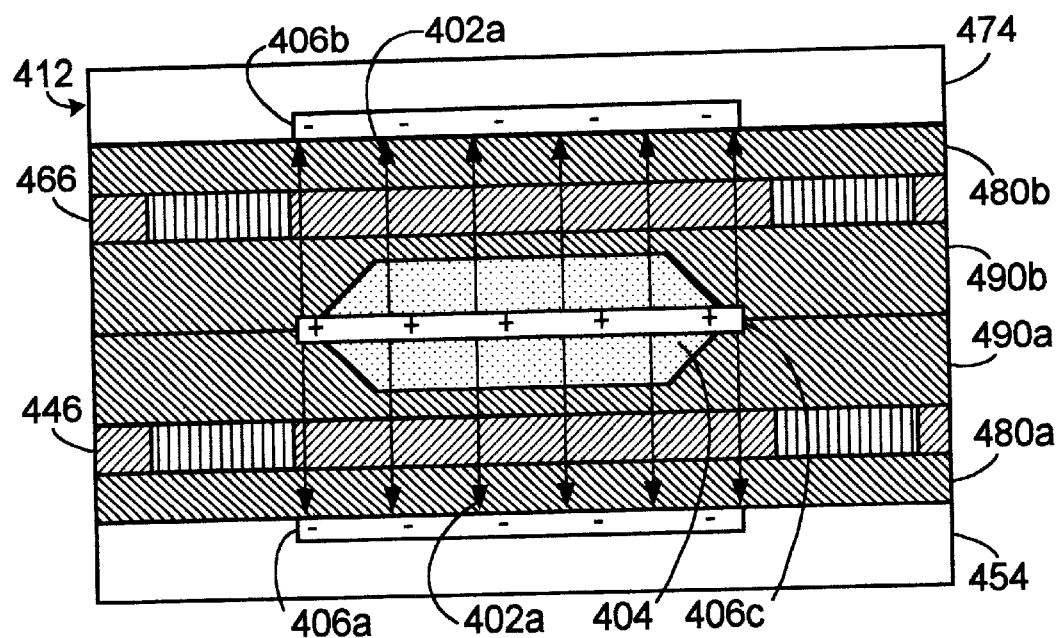
FIG. 5A is a cross-sectional view of an embodiment that may be used in modulating an electrical signal onto an optical signal.
Figure 5B:
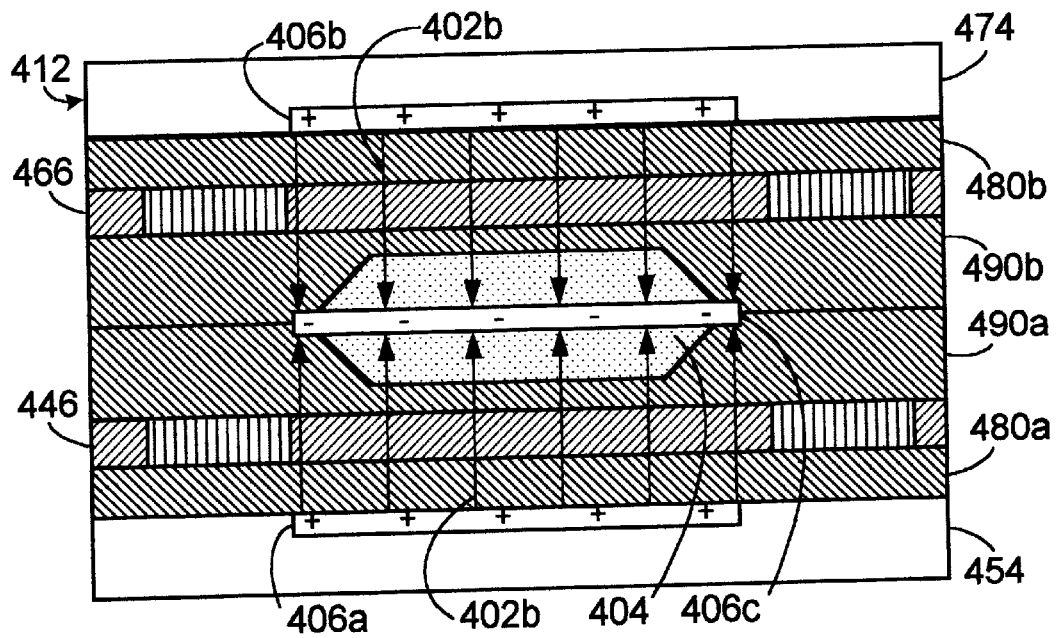
FIG. 5B is a cross-sectional view of the embodiment of FIG. 5A, wherein the electrical field has been reversed.

A transverse interferometer 412 of the type shown in FIGS. 5A and 5B could be employed as a means for optical signal modulation, as would be useful for telecommunications and high-speed data transmission. The field 402a,b could be generated by a two spaced-apart outer electrodes 406a,b and one central electrode 480c (all of which could comprise, for example, indium tin oxide). The outer electrodes 406a,b would be disposed between the substrates 454 and 474 and adjacent outer cladding layers 480a,b, respectively. The central electrode 480c would be disposed between two adjacent inner cladding layers 490a,b. Each of the outer electrodes 406a,b could be spaced apart across a relatively narrow distance from the central electrode 406c, thereby generating a strong electric field 402a,b, relative to the voltage applied to the electrodes 406a,b,c, and permitting a relatively high frequency electric field oscillation. When the material 404 within the cavity between the inner cladding layers 490a,b comprises an electro-optic material (which could be, for example, poly diacetylene) and the outer electrodes 406a,b have a polarity that is opposite from the central electrode 406c, the output becomes an oscillating optical signal having an intensity mimicking the oscillating electric field. Thus, the embodiment shown in FIGS. 5A and 5B could be used to modulate a signal from the electric field 402a,b onto an optical signal.

It is important to note that the above-described figures of the drawings disclosed herein are not drawn to scale. Certain features are exaggerated to aid in explaining the invention. Furthermore, the above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. An interferometer for detecting a property of an environment using a source of a beam of light, comprising:

a) a first planar waveguide having a first end, an opposite second end and a first interior surface, a first coupler disposed adjacent the first end so as to be capable of coupling a first portion of the beam from the source into the first planar waveguide and a second coupler disposed adjacent the second end so as to be capable of de-coupling a second portion of the beam from the first portion of the beam and onto a first predetermined exit path, a first region disposed along the first interior surface between the first coupler and the second coupler that allows light to propagate therethrough as a first function of exposure tot he enviroment disposed adjacent thereto;

b) a second planar waveguide having a third end, an opposite fourth end and a second interior surface, the second planar waveguide being disposed substantially parallel to the first planar waveguide so that a first portion of the first interior surface and a second portion of the second interior surface define a cavity therebetween, a second region disposed along the second interior surface between a third coupler and a fourth coupler that allows light to propagate therethrough as a second function, different from the first function, of exposure to the environment disposed adjacent thereto in the cavity defined between the first and the second planar waveguides, the third coupler disposed adjacent the third end so as to be capable of coupling a third portion of the beam into the second planar waveguide and the fourth coupler disposed adjacent the fourth end so as to be capable of de-coupling a fourth portion of the beam from the third portion of the beam and onto a second predetermined exit path, at least a portion of the second predetermined path being co-incident with at least a portion of the first predetermined path so as to form a combined beam; and c) a phase difference detector, responsive to the combined beam, that indicates a phase difference between the second portion of the beam and the fourth portion of the beam, so as to indicate the property of the environment.

2. The interferometer of claim 1, wherein the beam of light consists of a single mode.

3. The interferometer of claim 1, wherein the beam of light comprises a plurality of modes.

4. The interferometer of claim 1, wherein the first planar waveguide has a first exterior surface opposite the first interior surface and further comprising a first substrate disposed adjacent the first exterior surface.

5. The interferometer of claim 4, wherein the first substrate comprises a glass material.

6. The interferometer of claim 4, wherein the first substrate comprises silicon.

7. The interferometer of claim 6, wherein the first substrate comprises an alumina-gallium-arsenide material.

8. The interferometer of claim 1, wherein the second planar waveguide has a second exterior surface opposite the second interior surface and further comprising a second substrate disposed adjacent the second exterior surface.

9. The interferometer of claim 8, wherein the second substrate comprises glass material.

10. The interferometer of claim 8, wherein the second substrate comprises silicon.

11. The interferometer of claim 8, wherein the second substrate comprises an ralumina-gallium-arsenide material.

12. A method of manufacturing an interferometric device by applying a first waveguide onto a first surface of a first substrate so that the first waveguide has a first end and an opposite second end and disposing a first coupler adjacent the first end and a second coupler adjacent the second end, further comprising the steps of:

a) applying to a portion of the first waveguide a first treatment that allows light to propagate through the portion of the first waveguide as a first function of exposure to the environment adjacent the portion of the first waveguide;

b) applying a second waveguide onto a second surface of a second substrate so that the second waveguide has a third end and an opposite fourth end;

c) disposing a third coupler adjacent the third end and a fourth coupler adjacent the fourth end;

d) applying to a portion of the second waveguide a second treatment that allows light to propagate through the portion of the second waveguide as a second function, different from the first function, of exposure to the environment disposed adjacent the portion of the second planar waveguide; and e) disposing the first substrate substantially parallel to the second substrate so that the first coupler and the third coupler both lie on a first common optical path and so that the second coupler and the fourth coupler both lie on a second common optical path, the first common optical path and the second common optical path being at an angle to the direction of the first waveguide and the second waveguide, and so that the first surface and the second surface face each other and define a cavity, having a width, therebetween.

13. The method of claim 12, further comprising the step of placing a source of an optical beam adjacent the sensor so that an optical beam from the source is capable of entering the first waveguide through the first coupler and entering the second waveguide through the third coupler.

14. The method of claim 12, further comprising the step of placing a phase detector along the second common optical path.

15. The method of claim 12, wherein the step of applying to a portion of the first waveguide a first treatment includes a step of applying no treatment to the portion of the first waveguide.

16. The method of claim 12, further comprising the step of applying a cladding to both the first waveguide and the second waveguide.

17. The method of claim 16, wherein adjacent the first coupler and the second coupler the cladding has a thickness that is thicker than the cladding adjacent a portion of the first waveguide between the first coupler and the second coupler, so that the width of the cavity is a function of the thickness of the cladding adjacent the first coupler and the second coupler.

18. The method of claim 16, wherein adjacent the first coupler and the second coupler the cladding has a thickness that is thicker than the cladding adjacent a portion of the first waveguide between the first coupler and the second coupler and wherein adjacent the third coupler and the fourth coupler the cladding has a thickness that is thicker than the cladding adjacent a portion of the second waveguide between the third coupler and the fourth coupler, so that the width of the cavity is a function of the thickness of the cladding adjacent the first coupler, the second coupler, the third coupler and the fourth coupler.

* * * * *